(12) United States Patent
Sharratt

(10) Patent No.: US 8,303,531 B2
(45) Date of Patent: Nov. 6, 2012

(54) SPRAY APPLICATOR WITH POSITIONABLE SPRAY TIP

(75) Inventor: Todd W. Sharratt, Stillwater, MN (US)

(73) Assignee: Nordson Corporation, Westlake, OH (US)

( * ) Notice: Subject to any disclaimer, the term of this patent is extended or adjusted under 35 U.S.C. 154(b) by 748 days.

(21) Appl. No.: 12/369,069

(22) Filed: Feb. 11, 2009

(65) Prior Publication Data
US 2009/0199848 A1 Aug. 13, 2009

Related U.S. Application Data

(60) Provisional application No. 61/027,557, filed on Feb. 11, 2008.

(51) Int. Cl.
*A61M 37/00* (2006.01)
(52) U.S. Cl. ........................................................ 604/24
(58) Field of Classification Search .................... 604/24, 604/528; 606/108
See application file for complete search history.

(56) References Cited

U.S. PATENT DOCUMENTS

| 4,932,942 A | 6/1990 | Maslanka |
| 4,990,140 A | 2/1991 | Black |
| 5,484,408 A * | 1/1996 | Burns ..................... 604/102.02 |
| 6,974,411 B2 | 12/2005 | Belson |
| 7,172,552 B2 | 2/2007 | Wendlandt |
| 2005/0125002 A1* | 6/2005 | Baran et al. .................. 606/108 |

FOREIGN PATENT DOCUMENTS

JP 05168714 2/1993

* cited by examiner

*Primary Examiner* — Kevin C Sirmons
*Assistant Examiner* — Bradley Osinski
(74) *Attorney, Agent, or Firm* — Wood, Herron & Evans, L.L.P.

(57) ABSTRACT

An apparatus for applying a spray to a selected site on a patient includes a sheath having a through bore extending from a first end to a second end. A flexible multi-lumen tube is secured within the sheath and has a distal portion that extends beyond the second end of the sheath. A malleable wire is positioned within at least the distal portion of the multi-lumen tube wherein manual force is exerted upon the distal portion to position the distal end in a selected position by bending the malleable wire. A housing is attached to the rigid outer sheath and has a plurality of ports for engaging a multi-tube syringe and a port for injecting a gas into the selected site wherein each port is in communication with at least one lumen. A spray nozzle is removably attached to the distal end of the multi-lumen tube wherein the at least one liquid and the gas are discharged from the multi-lumen tube and into the spray nozzle such that the aerosol exiting the spray nozzle is effective in treating the selected site.

6 Claims, 9 Drawing Sheets

SPRAY APPLICATOR WITH POSITIONABLE SPRAY TIP

CROSS REFERENCE TO RELATED APPLICATION(S)

Figure 1:
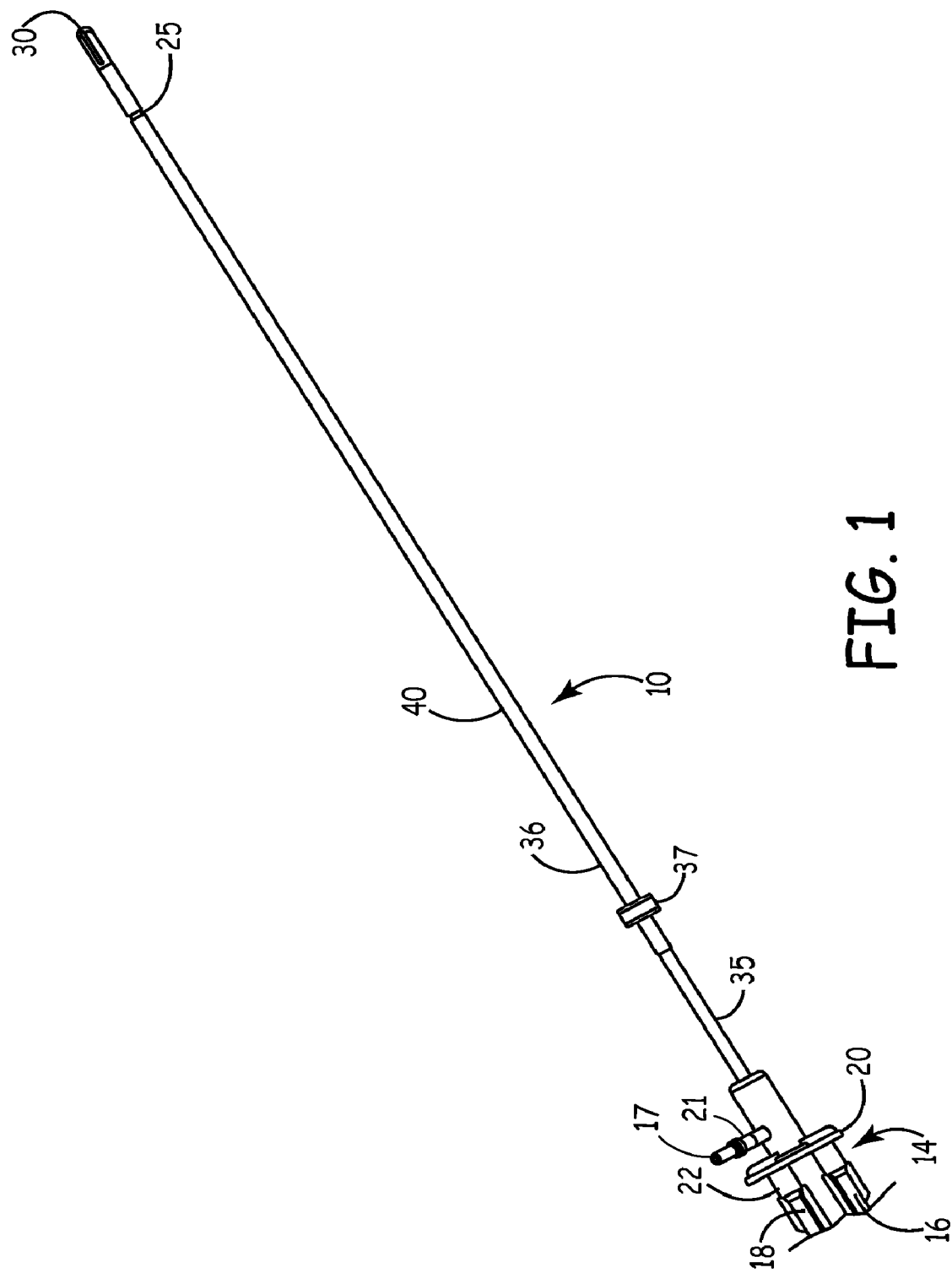
Figure 2:
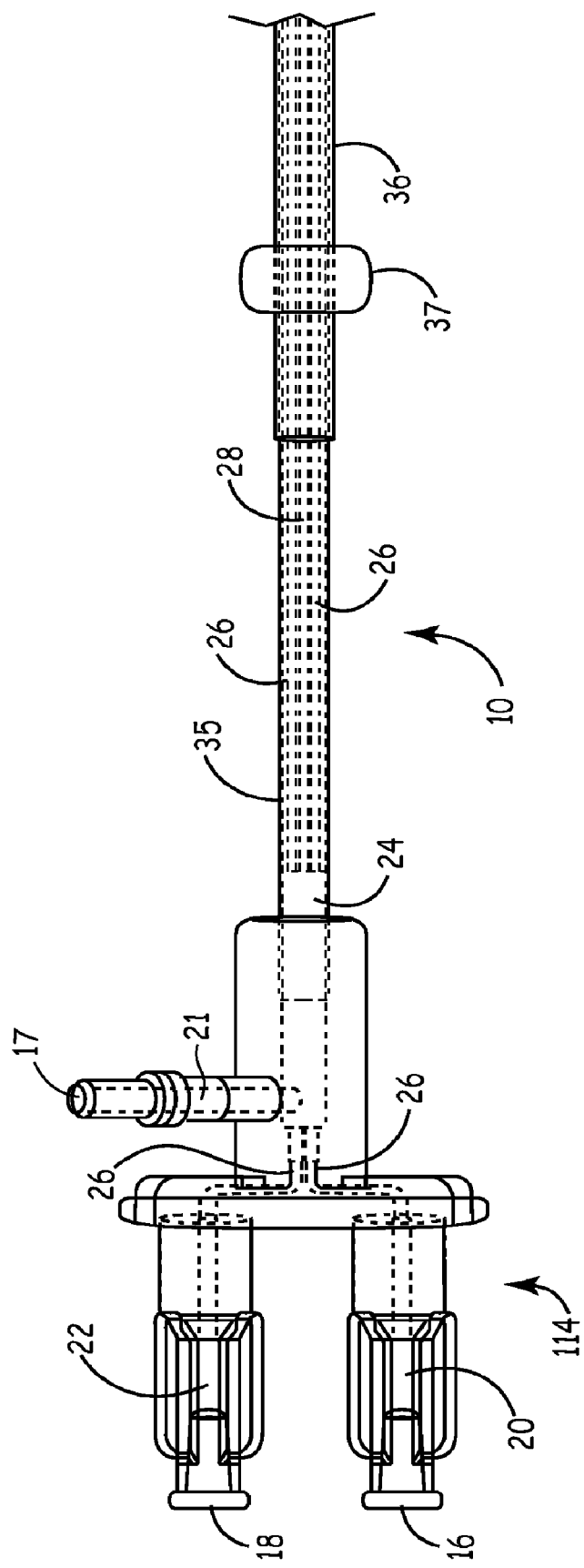
Figure 3:
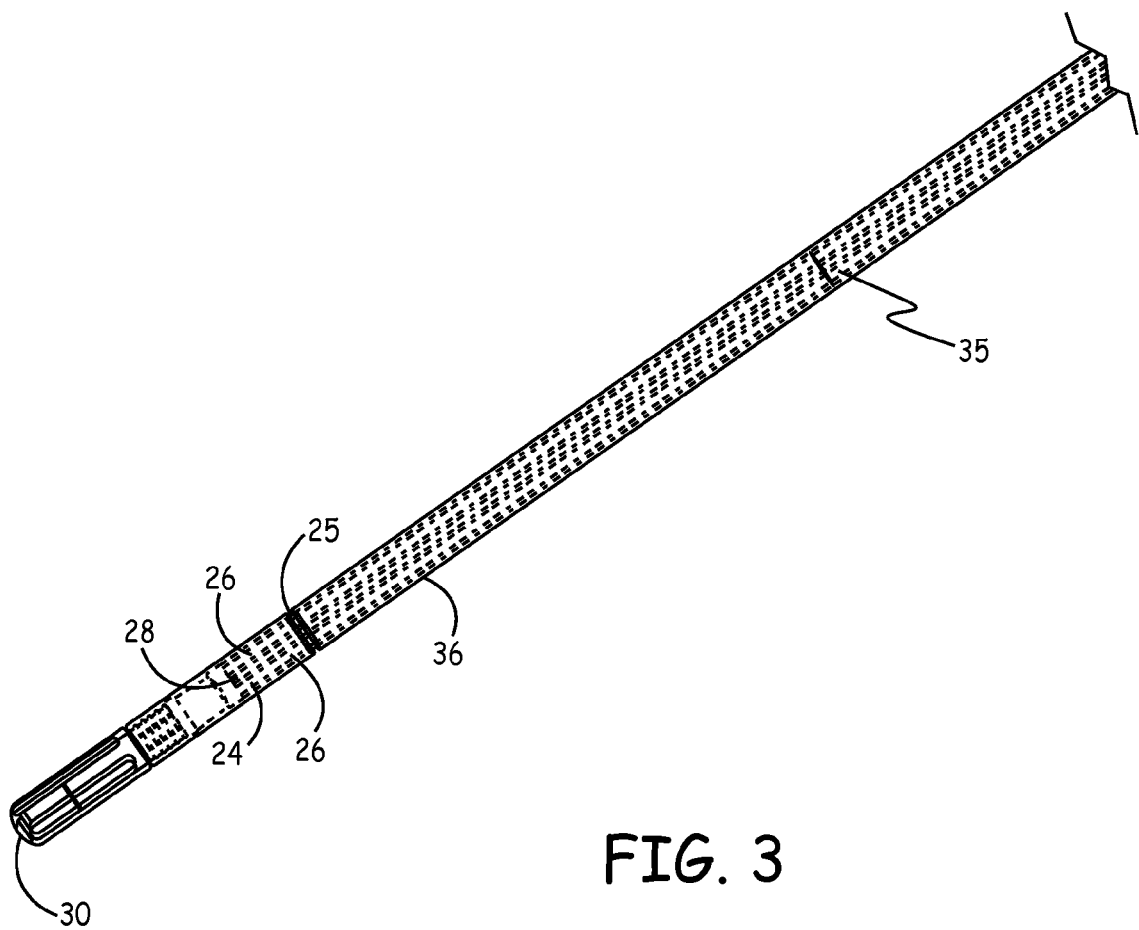
Figure 4:
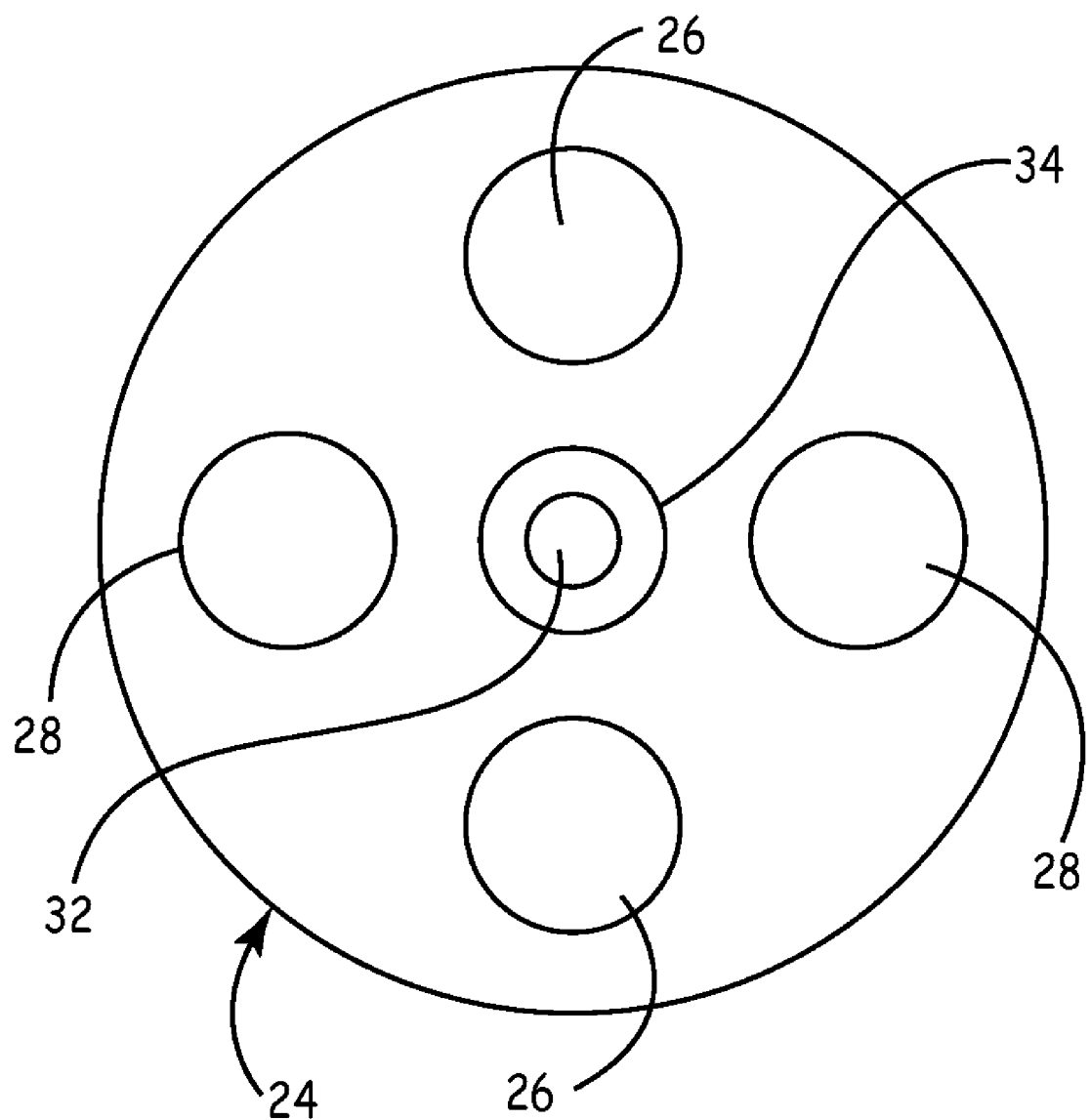

This application claims the benefit of U.S. Provisional Application Ser. No. 61/027,557 which was filed on Feb. 11, 2008, the contents of which are incorporated by reference in its entirety.

FIELD OF THE INVENTION

The present application relates to an applicator for applying a spray to a site on a patient's body. More particularly, the present invention relates to a spray applicator that can be manipulated to position a distal end in a selected position to deliver the spray to obstructed sites.

BACKGROUND OF THE INVENTION

Liquid spray applicators are utilized to deliver therapeutic aerosols, liquids and/or gas streams to anatomical surfaces within a surgical site of a patient. In the case of minimally invasive surgery, the surgical site may be artificially created in the body with lumen. It also may be desirable to deliver therapeutic aerosols to an open anatomical surface. The aerosol formulations may be delivered before a surgical procedure, after a surgical procedure, or during a surgical procedure.

Problems that physicians have encountered during surgical procedures include post operative pain, infections, tissue adhesions, and tumor formation. Numerous products addressing these issues exist on the market to improve the surgical or invasive experience and patient outcomes. Among these products are suction and irrigation wands that are used for flushing tissue sites with sterile water or saline and removing blood and other fluids.

A problem with delivering substances to anatomical surfaces in a body cavity is the inability to easily and effectively deliver and also control delivery to all or a portion of the surgical site. Among the difficulties associated with spraying of liquids the inability to reach all areas of a surgical site, especially where bleeding can be an operative issue. In some instances, a liquid is sprayed onto a surgical site to stop bleeding within a site. However, if the site cannot be reached by the spray applicator, the bleeding may continue through the procedure and until a natural clot is formed which can result in the excessive loss of blood as well as cause difficulties during the surgical procedure.

In some circumstances it may be desirable to direct an aerosol spray to certain areas within a cavity. The nozzles on many devices are fixed in orientation with respect to the instrument shaft. As a result, the caregiver must manipulate the shaft to direct the aerosol which can cause inefficiencies.

SUMMARY OF THE INVENTION

The present invention includes an apparatus for applying a spray to a selected site on a patient. The apparatus includes a sheath having a through bore extending from a first end to a second end. A flexible multi-lumen tube is secured within the sheath and has a distal portion that extends beyond the second end of the sheath. A malleable wire is positioned within at least the distal portion of the multi-lumen tube wherein manual force is exerted upon the distal portion to position the distal end in a selected position by bending the malleable wire. A housing is attached to the rigid outer sheath and has a plurality of ports for engaging a multi-tube syringe and a port for injecting a gas into the selected site wherein each port is in communication with at least one lumen. A spray nozzle is removably attached to the distal end of the multi-lumen tube wherein the at least one liquid and the gas are discharged from the multi-lumen tube and into the spray nozzle such that the aerosol exiting the spray nozzle is effective in treating the selected site.

BRIEF DESCRIPTION OF THE DRAWINGS

FIG. 1 is a perspective view of a spray applicator.

FIG. 2 is a schematic view of the housing of the spray applicator.

FIG. 3 is a schematic view of the distal end of the spray applicator.

FIG. 4 is a cross-sectional view of the multi-lumen tube of the spray applicator.

FIG. 5 is a top view of another spray applicator.

FIG. 6 is a plan view of the another spray applicator.

FIG. 7 is top view of the distal end of the another spray in a substantially straight configuration.

FIG. 8 is a top view of the distal end of the another spray applicator where the distal end is bent.

FIG. 9 is a perspective view and a sectional view of another embodiment of the multi-lumen tube of the present invention.

DETAILED DESCRIPTION OF THE ILLUSTRATIVE EMBODIMENTS

A spray applicator for applying an aerosol spray onto a surgical site is generally illustrated in FIG. 1 at 10. The spray applicator 10 has a distal end that is movable to direct the aerosol spray into a selected site on or in a patient.

Referring to FIGS. 1-4, the directional spray applicator 10 includes a housing 14 having parallel ports 16, 18 and side-port 17, the parallel ports 16, 18 are configured for attaching to a dual chamber syringe (not shown) where the ports 16, 18 can be utilized to transport one fluid or two fluids that are subsequently mixed together. The housing 14 includes passages 20, 21, 22 which connect to a multi-lumen tube 24 having separate lumens 26 for each of the different liquids and gases. The multi-lumen tube 24 also has lumens 28 for transferring a pressurized gas from the side-port 17 into a spray nozzle 30. The gas can be supplied from a pressurized container via side-port 117 and passage 121 as illustrated in FIG. 6 or the gas can be supplied from a sterilized air system that is commonly available at medical treatment facilities.

The spray nozzle is attached to a distal end 25 of the multi-lumen tube 24. As the liquids and gas enter the spray nozzle 30, a swirling or tornadic activity is created which mixes the two fluids sufficiently together to form a mixture that is effective for a selected purpose, such as stopping unwanted bleeding within the surgical site. The pressurized gas forces the liquids from the spray nozzle 30 and onto a selected surface within a patient's body. The passages 20, 22 within the housing 14 also include check valves (not shown) which prevent the gas from pressuring the liquid that are mixed together in the spray nozzle back into the syringe (not shown).

A pre-shaped memory wire 32, such as nitinol, is positioned with a central lumen 34 within the multi-lumen tube 24 which causes a distal portion 25 of the tube 24 to have a curved configuration such that the spray nozzle 30 can be directed at different angles which allows the spray to be applied to surfaces within a surgical site. A typical diameter of the pre-shaped wire is 0.028 inches although other diameter wires are also contemplated.

When no force is applied to a distal end of the multi-lumen tube 24, the pre-shaped memory wire 32 forces the distal end 25 of the multi-lumen tube 24 into a selected curved or bent configuration. The configuration of the distal portion 25 can be pre-determined by providing the memory wire with a pre-elected bend or curvature within the multi-lumen tube 24.

The multi-lumen tube 24 is typically encased within a rigid inner sheath 35 that extends from the housing 14 to proximate the distal end 25 of the tube 24 such that a segment of the multi-lumen tube 24 separates the distal end of the rigid inner sheath 35 and the spray nozzle 30. The rigid inner sheath 35 maintains the encased portion of the multi-lumen tube 24 in a substantially straight configuration.

A rigid outer sheath 36 is positioned over the rigid inner sheath 35 and has a length that is less than that of the rigid inner sheath 35. The rigid outer sheath 36 slides along a length of the inner rigid sheath 35 such that when the rigid outer sheath 36 is extended toward the spray nozzle 30, the rigidity of the outer sheath 36 straightens the pre-shaped memory wire 32 such that the spray nozzle 30 is substantially aligned with an axis 40 of the rigid inner sheath 35. An external collar 37 is positioned on the rigid outer sheath 36 to provide a gripping surface for moving the rigid outer sheath 36.

When the directional spray applicator 10 is positioned within the body, the operator can manually move the rigid outer sheath 36 towards a proximal end 12 of the applicator 10, thereby uncovering the distal portion 25 of the multi-lumen tube 24. By uncovering the distal end 25, the memory wire 32 forces the distal portion 25 of the multi-lumen tube 24 and the spray nozzle 30 into a selected angular position. Alternatively, the outer sheath 36 can be retained in a selected position and the rigid inner sheath 35 can be further inserted into the surgical site to remove force from the distal portion 25 of the multi-lumen tube to allow the spray nozzle 30 to be positioned at a selected angular position. As more of the distal portion 25 of the multi-lumen tube 24 is uncovered, the memory wire 32 forces the distal portion 25 into another selected position based upon the shape of the memory wire 32 that is substantially perpendicular to the axis 40 of the rigid inner sheath 35. Conversely, as less of the distal portion 25 of the multi-lumen tube 24 protrudes from the rigid outer sheath 35, the spray nozzle 30 is positioned at a more acute angle with respect to the axis 40 of the rigid inner sheath 35.

The inner sheath 35 also is rotatable within the outer sheath 36, such that the spray nozzle 30 can be rotated 360° around the axis 40 to spray a larger area within the surgical site. However, a non-rotatable slidable engagement of the outer sheath 36 and the inner sheath 35 is also contemplated.

Referring to FIG. 5-8, another spray applicator 110 can also utilizes a malleable wire 132 within a multi-lumen tube 124. One such malleable wire is an annealed 304 stainless steel that has a 0.028 inch diameter. However other diameter and materials of construction of the wire are also contemplated. By malleable is meant a wire that can be bent with manual force and retails a selected shape until a separate manual force is placed upon the wire.

Figure 5:
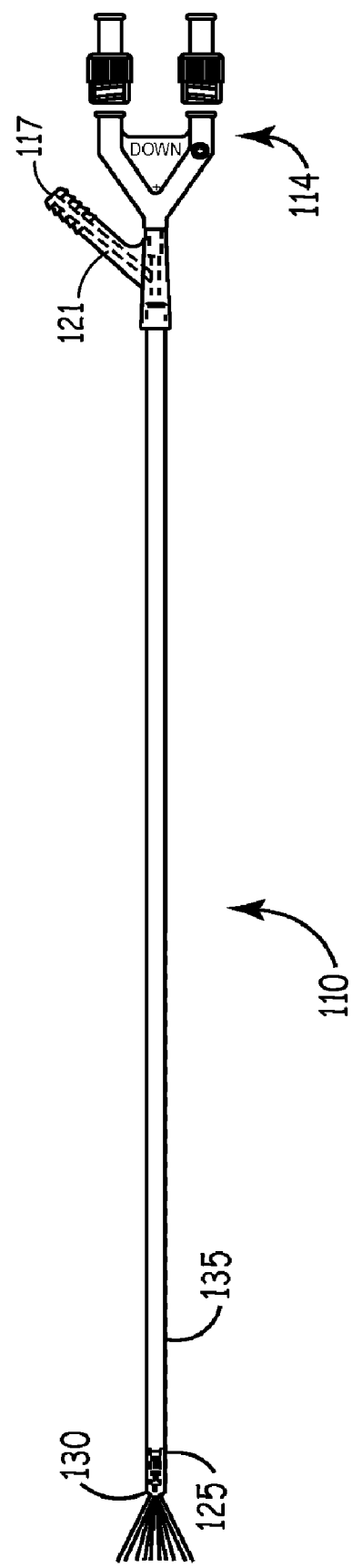
Figure 6:
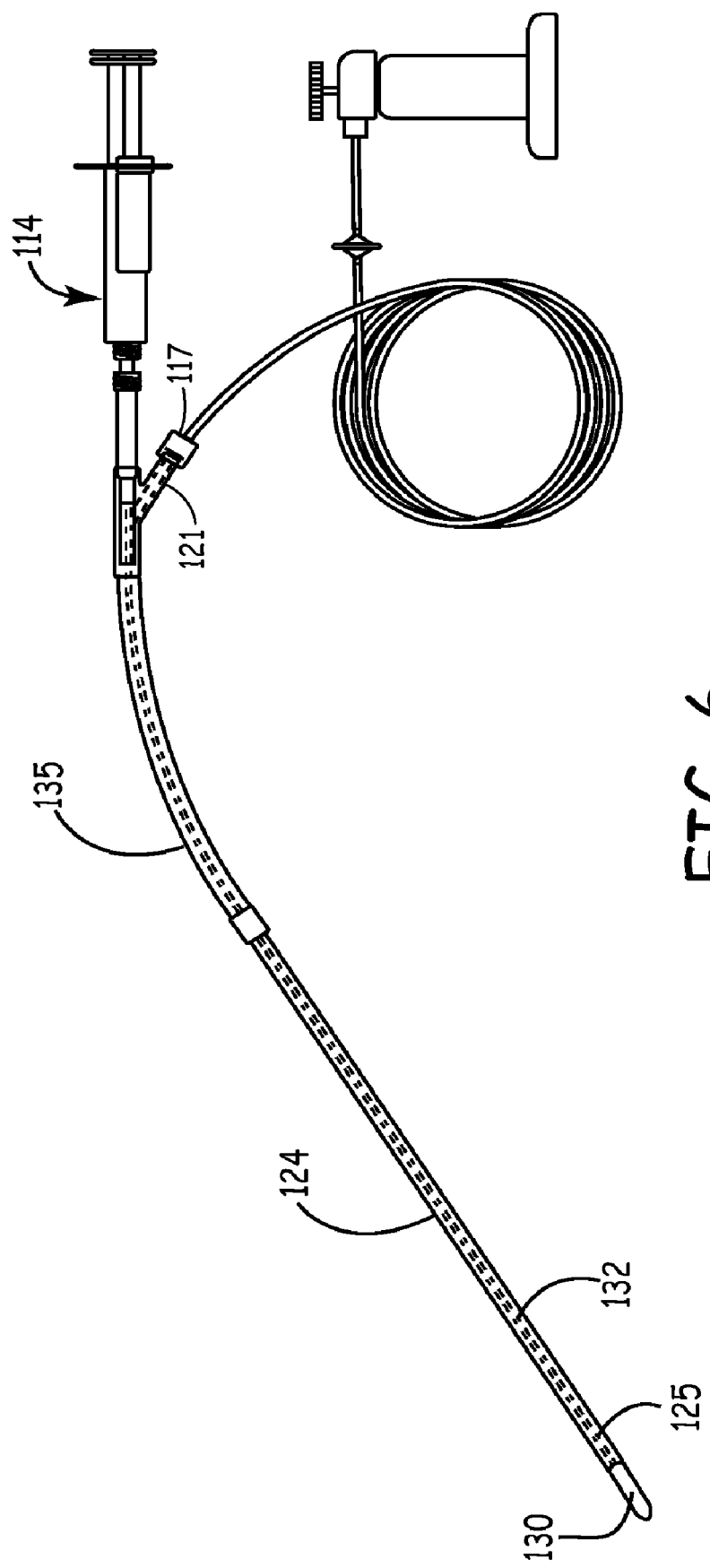
Figure 7:
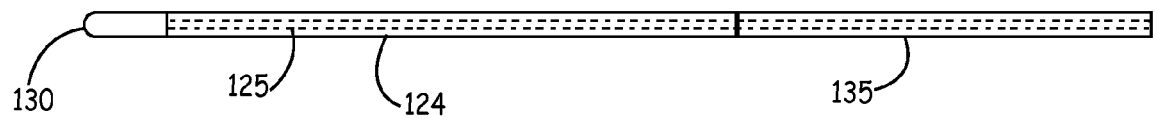
Figure 8:
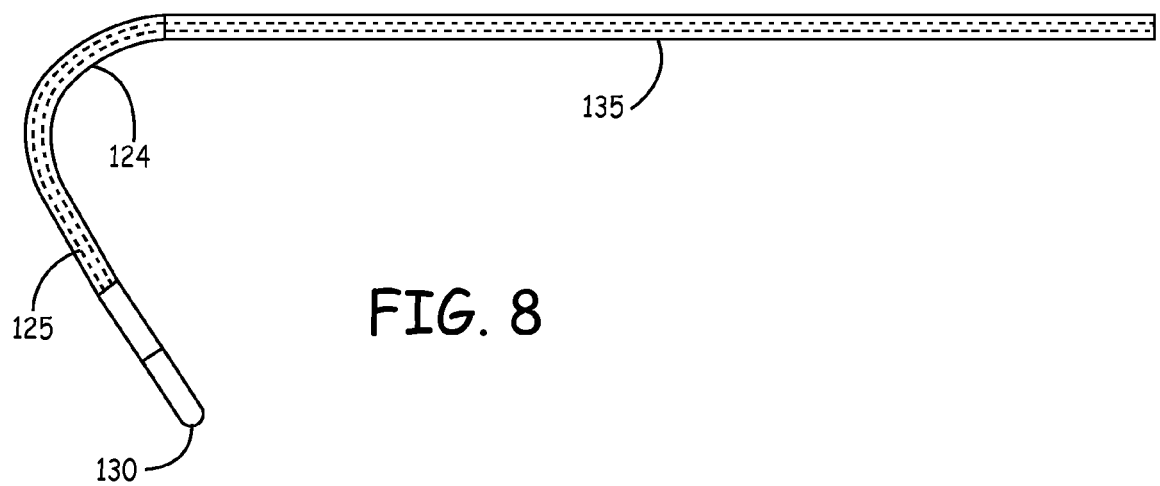

The applicator 110 includes a housing 114 having the same or similar configuration to that of housing 14. The multi-lumen tube 124 is flexible and is positioned within a sheath 135, which may be either rigid or flexible. A distal end 125 of the multi-lumen tube 124 extends from the sheath 135 and has a spray nozzle 130 attached to the distal end 125 as shown in FIG. 6. Alternatively, the sheath 135 may extend to the spray nozzle 130 as shown in FIG. 5 provided the sheath 135 is flexible.

The applicator 110 operates in a manner substantially the same as the applicator 10. However, to position the spray nozzle 130 in a selected position, manual force is exerted upon the multi-lumen tube 124 and/or the sheath 135 to bend the malleable wire 132. The malleable wire 132 retains the spray nozzle 130 in a selected position from a straight configuration in FIG. 7 to a bent or angular configuration in FIG. 8 such that a spray can be directed to a selected area in a surgical site.

Figure 9:
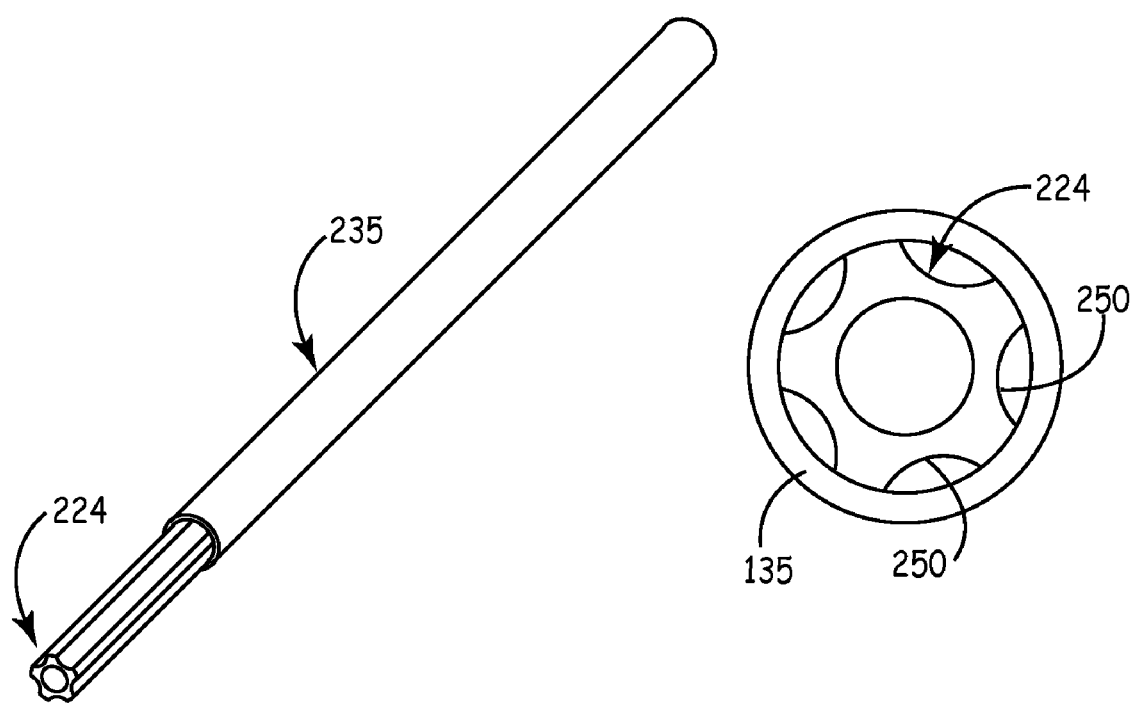

Another configuration of a multi-lumen tube 224 is illustrated in FIG. 9. The multi-lumen tube 224 includes arcuate cross sectional indentions 250 extending along at least a partial length of the tube 224. The multi-lumen tube 224 is positioned within a sheath 135. The perimeter edges 225 and an inner surface of the sheath 137 form lumens 257 and a hermetic seal between the lumens 257 to prevent cross-contamination of liquids and/or liquids and gases between the lumens 257. Positioning lumens 257 at an exterior of the tube 224 prevents the cross-sectional area of the lumens 257 from being reduced as the tube 224 is bent and thereby ensures a more reliable delivery of the liquids and gases to the surgical site.

Although the present invention has been described with reference to preferred embodiments, workers skilled in the art will recognize that changes may be made in form and detail without departing from the spirit and scope of the invention.

What is claimed is:

1. An apparatus for applying a spray to a selected site on a patient comprising:
   an outer sheath for positioning through a surgical access port, the outer sheath having a through bore extending from a proximal end to a distal end along an axis thereof; and
   a catheter positioned through the through bore of the outer sheath, the catheter being slidable and rotatable within the outer sheath, the catheter comprising:
      a rigid inner sheath having a through bore extending from a first end to a second end, the second end being distal to the first end;
      a flexible multi-lumen tube secured within the through bore of the inner sheath and having a pre-shaped distal end portion extending distally away from at least the second end of the inner sheath; and
      a spray nozzle removably attached to a distal end of the multi-lumen tube and configured such that when at least one liquid and a gas are discharged from the multi-lumen tube and into the spray nozzle a tornado effect creates a desired spray such that the spray exiting the spray nozzle is effective in treating the selected site,
   wherein the rigid inner sheath is configured to maintain at least a proximal portion of the multi-lumen tube in a straight configuration and distal movement of the outer sheath relative to the multi-lumen tube transitions the pre-shaped distal end portion of the multi-lumen tube from a curved configuration to a straight configuration; and
   wherein the spray nozzle has a diameter that is greater than a diameter of the through bore in the outer sheath which prevents the spray nozzle from entering the through bore of the outer sheath and which prevents blockage of the through bore in the outer sheath.

2. The apparatus of claim 1 and further comprising a housing attached to the first end of the inner sheath and having a plurality of ports, a first portion of the plurality of ports configured for engaging a multi-tube syringe, wherein each port of the first portion of the plurality of ports is in fluidic communication with at least one lumen of the multi-lumen tube, and a second portion of the plurality of ports is configured for communicating with a gas source, wherein each port of the second portion of the plurality of ports is in fluidic communication with at least one lumen of the multi-lumen tube.

3. The apparatus of claim 1 and further comprising a preformed memory shaped wire positioned within at least one lumen of the multi-lumen tube to pre-shape the distal end portion thereof.

4. The apparatus of claim 3 and wherein the preformed memory shaped wire comprises a nickel-titanium wire.

5. The apparatus of claim 1 and wherein the multi-lumen tube comprises a five lumen tube having a central lumen and four evenly spaced lumens positioned about the central lumen.

6. The apparatus of claim 5 and wherein a preformed memory shaped wire is positioned within the central lumen.

* * * * *